US00PP07953P

United States Patent [19]

Bradford et al.

[11] Patent Number: Plant 7,953

[45] Date of Patent: Aug. 25, 1992

[54] PEACH TREE (CRIMSON LADY)

[76] Inventors: Lowell G. Bradford, 12439 E. Savana Rd.; Norman G. Bradford, 11875 E. Savana Rd., both of Le Grand, Calif. 95333

[21] Appl. No.: 646,262

[22] Filed: Jan. 28, 1991

[51] Int. Cl.[5] ..... A01H 5/00
[52] U.S. Cl. ..... Plt./43.1
[58] Field of Search ..... Plt./43

[56] References Cited

U.S. PATENT DOCUMENTS

P.P. 3,165 5/1972 Anderson ..... Plt. 41

*Primary Examiner*—James R. Feyrer

[57] ABSTRACT

The present invention relates to a peach tree and more particularly to a new and distinct variety broadly characterized by a large size, vigorous, hardy, productive and regular bearing tree. The fruit matures under the ecological conditions described approximately the first week in June, with first picking on June 3, 1990. The fruit is uniformly large in size, excellent in flavor, attractively globose in shape, clingstone in type, very firm and nonmelting in texture, and almost full red in skin color. The variety was developed by crossing two unnamed peach seedlings, the seed parent having Red Diamond (U.S. Plant Pat. No. 3,165) nectarine as its seed parent and Springcrest (unpatented) peach as its pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of peach tree, which has been denominated varietally as "Crimson Lady". The present variety was hybridized in 1984 by us in a cultivated area of our experimental orchard at Bradford Farms near Le Grand, Calif. in Merced County (San Joaquin Valley). It was developed by crossing two unnamed peach seedlings, the seed parent having Red Diamond (U.S. Plant Pat. No. 3,165) nectarine as a seed parent and Springcrest (unpatented) peach as a pollen parent. Subsequent to origination of the present variety of peach tree, we asexually reproduced it by budding and grafting, and such reproduction of plant and fruit characteristics were true to the original plant in all respects.

The fruit produced by the present peach variety most closely resembles one of its grandparents, Springcrest (unpatented) peach, by being large in size, heavy in production, and early maturing, but is distinguished therefrom and an improvement thereon by having almost full red skin color at ripening time, by being clingstone in type, by having excellent sweet flavor, by ripening 7 days later, and by being extremely firm and non-melting in texture.

The present variety exhibits desirable characteristics common to its other grandparent, Red Diamond (U.S. Plant Pat. No. 3,165) nectarine, by producing firm fruit that is nearly full red at harvest time, but noticeably differs by being a peach instead of a nectarine, by being clingstone instead of freestone, by having a large blossom instead of a small blossom, and by ripening about 28 days earlier.

DRAWING

The accompanying photograph displays the characteristics of the whole fruit in skin color and form, a characteristic fruit divided transversely to its axial diameter showing the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of hard eating ripe on Jun. 7, 1990. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Productive.
Bearing: Regular bearer.
Trunk:
- *Size.*—Medium.
- *Texture.*—Medium.
- *Bark color.*—Moderate brown [58. m.Br].
- *Lenticels.*—Numerous. Color: Brownish orange [54. brO]. Size: ⅛" to ¼", [3.2-6.4 mm.].

Branches:
- *Size.*—Medium.
- *Texture.*—Medium.
- *Color.*—1st Year Wood Topside: Grayish pink [8. gy.Pk]. 1st Year Wood Underside: Brilliant yellow green [116. brill.YG]. Older Wood: Grayish brown [61. gy.Br].
- *Lenticels.*—Numerous, very small.

Leaves:
- *Size.*—Large. Average length: 6⅛" [155.6 mm.]. Average width: 1 5/16" [33.3 mm.].
- *Thickness.*—Medium.
- *Form.*—Elliptical.
- *Apex.*—Acuminate.
- *Base.*—Acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ⅜" [9.5 mm.]. Average Thickness: 3/32" [2.4 mm.]. Dorsal Color: Strong yellow green [117. s.YG]. Ventral color: Moderate yellow green [120. m.YG].

*Stipules.*—Numerous. Average Length: ¼" [6.4 mm.].

*Glands.*—Numbers: Mostly 2 per leaf. Position: Mostly oppositely positioned on petiole and base of blade. Size: Small. Form: Globose. Color: Light reddish brown [42. l.rBr].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Large.

*Color.*—Pale pink [7. p.Pk].

FRUIT

Maturity when described: Firm and eating ripe, Jun. 7, 1990.

Date of first picking: Jun. 3, 1990.

Date of last picking: Jun. 16, 1990.

Size: Uniform, large.

*Average diameter axially.*—2¾" [69.9 mm].

*Average traversely in suture plane.*—2⅝" [66.7 mm].

Form: Uniform, symmetrical, globose with some slight truncation at the base.

*Longitudinal section form.*—Round.

*Transverse section through diameter.*—Round.

Suture: An inconspicuous shallow line extending from the base to the apex, with a slight depression beyond the pistil point.

Ventral surface: Rounded, lipped very slightly throughout on one side.

Lips: Slightly unequal.

Cavity: Flaring, elongated in the suture plane, suture showing on one side only.

Base: Slightly truncate.

Apex: Rounded.

Pistil point: Mostly oblique, short in length.

Stem: Medium.

*Average length.*—⅜" [9.5 mm.].

*Average width.*—⅛" [3.2 mm.].

Skin:

*Thickness.*—Medium.

*Texture.*—Medium.

*Tenacity.*—Tenacious to flesh.

*Tendency to crack.*—None observed as of yet.

*Color.*—Dark red [16. d.R] smoothly blended into a dark yellowish pink [30. d.yPk] background.

Down: Scant, short, does not roll up when rubbed.

Flesh:

*Color.*—Brilliant yellow [83. brill.Y] to the stone.

*Amygdalin.*—Moderate.

*Juice.*— *Abundant, rich.*

*Texture.*—Very firm, non-melting.

*Fibers.*—Abundant, fine, tender.

*Ripens.*—Almost evenly, but slightly earlier at the apex.

*Flavor.*—Mild and very sweet.

*Aroma.*—Distinct.

*Eating quality.*—Very best.

STONE

Type: Clingstone.

Form: Oval.

Base: Oblique.

Apex: Acute with a sharp point.

Sides: Equal.

Surface: Irregularly furrowed toward the apex and pitted near the base.

Ridges: Rounded.

Color: Pale orange yellow [73. p.OY].

Pit wall: ¼" [6.4 mm.] thick.

Tendency to split: Very slight.

Kernel:

*Form.*—Oval.

*Taste.*—Very bitter.

*Viable.*—Yes.

*Average width.*—⅜" [9.5 mm.].

*Average length.*—⅝" [15.9 mm.].

Pellicle color: Deep yellowish brown [75. deep yBr].

Amygdalin: Abundant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of peach tree possesses the described characteristics under the ecological conditions at Le Grande, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, which most nearly resembles its grandparent, Springcrest (unpatented), by producing peaches that are large in size, heavy in production, and early maturing, but is distinguished therefrom and an improvement thereon by having almost full red skin color at ripening time, by being clingstone instead of freestone in type, by having a sweeter flavor, by ripening 7 days later, and by being extremely firm and non-melting in texture.

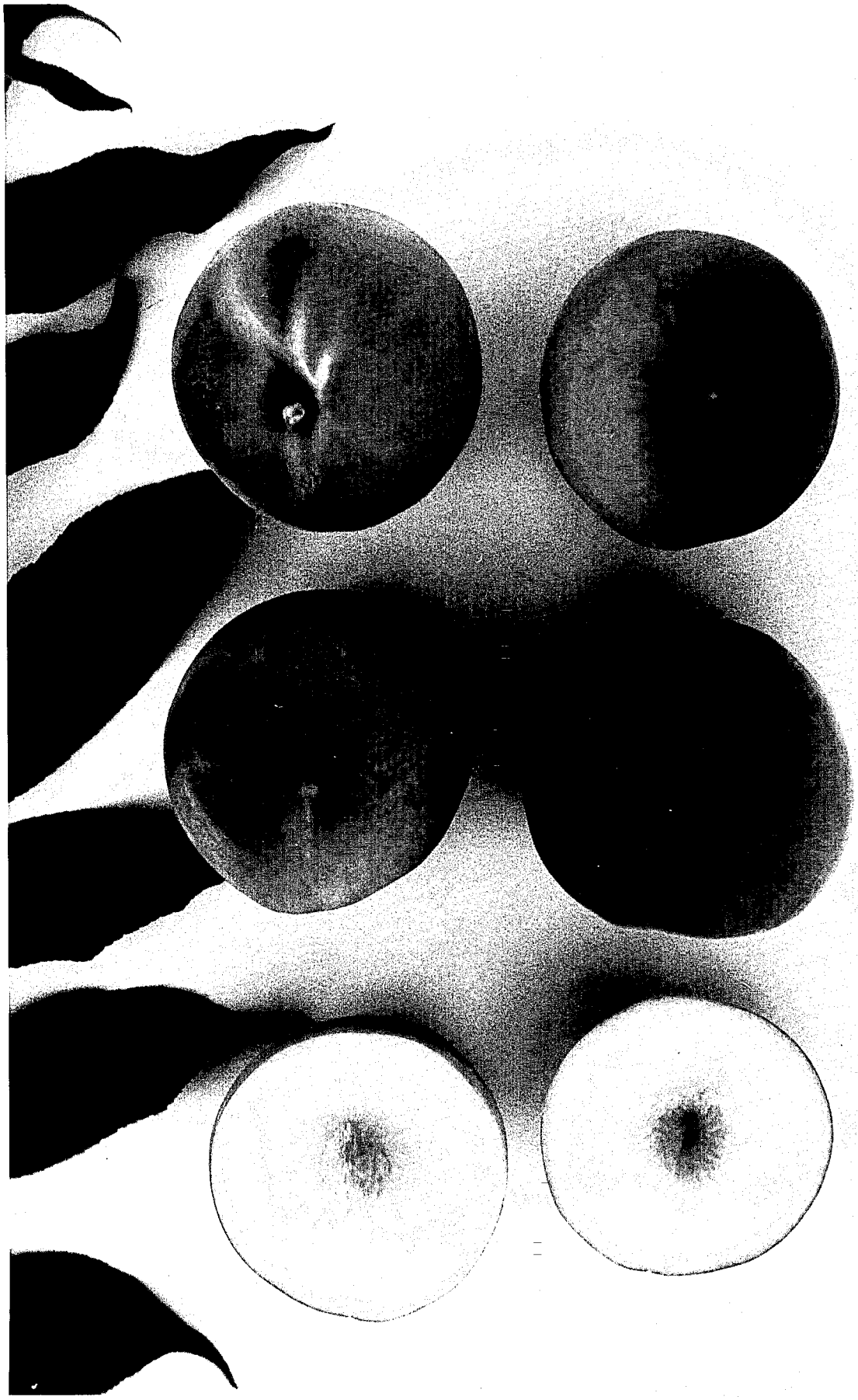

* * * * *